United States Patent
Letts

(10) Patent No.: US 8,700,432 B2
(45) Date of Patent: Apr. 15, 2014

(54) METHOD AND SYSTEM FOR CUTANEOUS MEDICINE DIAGNOSTICS

(76) Inventor: Gary A. Letts, Stamford, CT (US)

( * ) Notice: Subject to any disclaimer, the term of this patent is extended or adjusted under 35 U.S.C. 154(b) by 58 days.

(21) Appl. No.: 13/051,752

(22) Filed: Mar. 18, 2011

(65) Prior Publication Data

US 2011/0231205 A1      Sep. 22, 2011

Related U.S. Application Data

(60) Provisional application No. 61/315,724, filed on Mar. 19, 2010.

(51) Int. Cl.
- G06F 7/04 (2006.01)
- G06F 15/16 (2006.01)
- G06F 17/30 (2006.01)
- H04L 29/06 (2006.01)

(52) U.S. Cl.
USPC .................................. 705/3; 705/2

(58) Field of Classification Search
USPC ......................................................... 705/2–3
See application file for complete search history.

(56) References Cited

U.S. PATENT DOCUMENTS

| | | | | |
|---|---|---|---|---|
| 6,944,491 | B2 | 9/2005 | Leveque | 600/407 |
| 6,993,167 | B1 * | 1/2006 | Skladnev et al. | 382/128 |
| 7,457,659 | B2 | 11/2008 | Maschke | 600/431 |
| 2002/0016720 | A1 * | 2/2002 | Poropatich et al. | 705/3 |
| 2002/0103854 | A1 * | 8/2002 | Okita | 709/203 |
| 2002/0161605 | A1 * | 10/2002 | Newman et al. | 705/2 |
| 2005/0065813 | A1 * | 3/2005 | Mishelevich et al. | 705/2 |
| 2005/0119551 | A1 * | 6/2005 | Maschke | 600/407 |
| 2005/0251415 | A1 * | 11/2005 | Pak | 705/2 |
| 2008/0275315 | A1 | 11/2008 | Oka et al. | 600/306 |
| 2009/0060304 | A1 | 3/2009 | Gulfo et al. | 382/128 |
| 2009/0245603 | A1 * | 10/2009 | Koruga et al. | 382/128 |
| 2009/0279760 | A1 | 11/2009 | Bergman | 382/128 |
| 2010/0302358 | A1 | 12/2010 | Chen et al. | 348/77 |

OTHER PUBLICATIONS

Romero et al., Telemedicine and Teledermatology (I): Concepts and Applications, 2008, Actas Dermo-Sifiliograficas (English Edition), vol. 99, Issue 7, pp. 506-522.*
Telemedicine and Teledermatology (I): Concepts and Applications, 2008, Actas Dermo-Sifiliograficas (English Edition), vol. 99, Issue 7, pp. 506-522.*
International Preliminary Report on Patentability dated May 14, 2012 corresponding to International Patent Application No. PCT/US11/29044.
International Search Report dated May 19, 2011 from corresponding PCT/US2011/029044.
The Dark Intelligence Group, Inc., *"Do It Yourself" Dermatopathology Will Use Consumer's Cell Phone Images*, Mar. 15, 2010, 4 pages. http://www.businesswire.com/portal/site/home/permalink/?ndmViewI . . . , *"Halfpenny Technologies Introduces Mobile Connectivity Solution to Provide Physicians with 24/7 Smartphone Access to Lab Results"*; Dec. 15, 2009, 2 pages.

* cited by examiner

*Primary Examiner* — Joy Chng
(74) *Attorney, Agent, or Firm* — Ohlandt, Greeley, Ruggiero and Perle, L.L.P.

(57) ABSTRACT

There is provided a system for cutaneous diagnosis including a first access device. The first access device includes a camera, a processor and a display of digital body map having an anatomical marker. The camera captures image data of a lesion and the processor tags a location of the lesion captured from the camera with the anatomical marker, yielding a first record. The first record is transmitted by the first access device via a network to the first database. The first database receives and stores the first record. The second access device is in communication with the database. The second access device retrieves the first record from the database via the network and attaches physician data to the first record, thus yielding a second record. The second record is transmitted via the network to a second database and is stored therein.

17 Claims, 19 Drawing Sheets

Adding tag and photo

215

Insurance info

215

METHOD AND SYSTEM FOR CUTANEOUS MEDICINE DIAGNOSTICS

CROSS-REFERENCE TO RELATED APPLICATIONS

The present application is claiming priority of U.S. Provisional Patent Application Ser. No. 61/315,724, filed on Mar. 19, 2010, the content of which is herein incorporated by reference.

BACKGROUND

1. Field of the Disclosure

The present disclosure relates to diagnosis of patients, and more particularly, to a method and system for cutaneous medicine diagnostics.

2. Description of the Related Art

In the background art, there is lacking a system that aggregates patient's own observations, signs and symptoms, clinical data, and histopathology data for a patient's dermatological conditions. Conventional medical practice for tracking and diagnosing of dermatological conditions is typically confined to a review of lesions during periodic office visits to the dermatologist. The disadvantage of such periodic office consultations is that it fails to aggregates patient's own observations, signs and symptoms, clinical data, and histopathology data for a patient's dermatological conditions. Moreover, such conventional systems are incapable of integrating all of the above data into a physician's diagnosis, which leads to disadvantages to the patient, to the patient's treating physician, and to a consulting pathologist.

First, the conventional office consultation procedure for diagnosing patients is static, i.e., they only can compare against a prior office consultation and does not provide the benefit of historical changes to the lesion between consultations. There is limited availability of sequential pictorial and clinical information about disease progression in the same patient in the background art: for the training of physicians, particularly dermatologists and dermatopathologists, this is a distinct disadvantage. Dermatological lesions evolve over time. Lesions acquire and lose key features that influence a diagnosis. A dermatologist who encounters a lesion very early or very late in the evolution of that lesion may be less likely to or even unable to diagnose the lesion accurately, particularly after a single encounter and in some cases even with histological support. Dermatologists are taught to recognize the different stages of a lesion by reviewing photographs of lesions from the same disease, present and documented most often in different patients, but at various stages of development. The evolution of a given lesion is now represented primarily as composite sequential photographs from different patients. Within the confines of systems of the background art, the logistics of documenting the same lesion in one patient over the course of its evolution are difficult to overcome due to the variance with which patients seek or can receive medical attention versus the pace at which lesions from different categories change. An evolving lesion can be very difficult to diagnose if the key diagnostic features wax and wane as they often do, or if the key diagnostic features are partially developed or in regression at the time of evaluation. This renders dermatology more difficult to learn for clinicians and pathologists alike, and limits the accuracy of diagnoses, particularly in the early and late stages of many skin conditions. Patients are sometimes, therefore, required to make multiple visits, or to begin a possibly-erroneous presumptive treatment before an accurate diagnosis is reached.

Second, there is lacking in the background art a system that tracks changes over time in a skin lesion, as related to a scope of differential diagnosis of the lesion by the clinician. Sequential photographs may be useful for following gross changes, but have a shortcoming in that they can mask relatively small, subtle changes due to variable magnification and focal point, making evaluation of lesion progression more difficult. Although patients might be very interested in their own skin care, patients have no easy way of monitoring all their skin changes or lesions all the time, in a fashion that rewards the patient for being involved in their own skin care or that brings additional descriptive and sometimes key diagnostic information to the dermatologist or pathologist. This is especially so when an office visit is delayed and the diagnostic features of the lesion are no longer present at the time of evaluation as is the case of many inflammatory lesions. In addition, many patients lack a detailed medical vocabulary to describe succinctly, skin changes in a way that would be additionally useful to a dermatologist in resolving a difficult differential diagnosis.

Third, the background art lacks a mechanism for patients to communicate with, interact with or choose the best or a preferred dermatopathologist to initially interpret the stained tissue sections produced from their biopsy in order to render a diagnosis. Patients currently do not have a simple, reliable way to evaluate and choose the best laboratory to process their skin biopsies or evaluate or choose the ideal dermatopathologist for rendering a diagnosis, in the same way that they evaluate and choose a dermatologist, surgeon or primary care doctor. The dermatopathologist renders the diagnosis on which medical treatment, surgical procedures and prognoses are based. Currently, in many cases, third party payers (e.g., insurance providers) decide where the patient's biopsy specimens are sent for laboratory processing and therefore by whom dermatopathology consultation is performed, and this is often based on exclusive, pre-negotiated contracts between the third party payers and the large national laboratories that employ a growing number of dermatopathologists. Alternatively the dermatologist may decide where the patient's biopsies are sent based on prior relationships with the dermatopathologists, relationships often established during their residency and fellowship, or based on the reputation and track record of the dermatopathologist. Dermatopathologists who practice independently have no easy way to demonstrate their advanced training or expertise directly to the patient. Communication between the dermatopathologist and with the ordering dermatologist is also limited to telephone calls and faxes, email or online lookup of results, all of which are inconvenient in that they require interruption of workflow by either the pathologist or the dermatologist. Further, dermatopathologists have almost no way of seeing the evolution of a skin lesion or the static lesion at the time it is biopsied, unless the dermatologist is inclined to take a photograph and email it to the dermatopathologist or upload it to a laboratory information system, which is a non-trivial addition to the logistics of a patient's visit. A lack of this clinical information can further increase the chances of a late or improper diagnosis. This gross appearance of a lesion is lost at the time of the biopsy if not captured by photography, due to changes in the devitalized tissue as well as other changes secondary to chemical processing of the tissue in preparation for the microscopic evaluation.

Fourth, the background art leaves practitioners limited in their ability to undertake remote diagnosis and advisement of patients who cannot be physically present with a clinician for a skin exam.

SUMMARY

There is provided a system for cutaneous diagnosis including a first access device, a first database and a second database. The first access device includes a camera, a processor and a display of digital body map having an anatomical marker. The camera captures image data of a lesion and the processor tags a location of the lesion captured from the camera with the anatomical marker, thus yielding a first record. The first database is in communication with the first access device via a network. The first record is transmitted by the first access device via the network to the first database. The first database receives and stores the first record. The second access device is in communication with the database. The second access device retrieves the first record from the database via the network and attaches physician data to the first record, thus yielding a second record. The second record is transmitted via the network to a second database and is stored therein.

In some embodiments, the second record is transmitted via the network to a third access device. A diagnosis of the lesion is generated and associated with the second record, thus yielding a third record. The diagnosis may include a diagnosis of the lesion, gross details of the lesion, microscopic details of the lesion, test results from a skin biopsy, histological images that corresponds to the clinical image at the time of the biopsy, and combinations thereof. The third can be transmitted via the network to a third database and stored in the third database. The first database, the second database and the third database may be a single database. Typically, the third record is accessible by access devices, e.g., access device 105, 106, 107. In some embodiments, an appropriate security clearance or other appropriate identification is required before the third record is retrieved.

A computer implemented method for cutaneous diagnosis is also provided. The method includes imaging a lesion with a first access device, providing a digital body map having an anatomical marker to the first access device, associating the anatomical marker with the image data, thus yielding a first record. Transmitting the first record from the first access device to a database and storing the first record in a database. Transmitting the first record via from the database to a second access device and attaching physician data to the first record via the second access device, thus yielding a second record. Transmitting the second record to a second database and storing the second record in the second database.

A storage medium having instructions is also disclosed. The instructions, when read by a processor, cause the processor to image a lesion with a first access device, provide a digital body map having an anatomical marker to the first access device, and associate the anatomical marker with the image data, thus yielding a first record. The instructions further cause the processor to: transmit the first record from the first access device to a database, store the first record in a database, transmit the first record via from the database to a second access device, and attach physician data to the first record via the second access device, thus yielding a second record. The instructions further cause the processor to transmit the second record to a second database and store the second record in the second database An additional method to for historically monitoring a lesion is provided. The method includes providing a digital body map, receiving avatar data including an anatomical marker associated with a location of a lesion on the digital body map. Receiving image data of the lesion; associating the avatar data and the image data, thus yielding a record. Storing the record in a database, receiving additional image data, associating the avatar data and the additional image data, thus yielding a second record; storing the first record and the second record as a patient profile in the repository and retrieving the patient profile as a result of receiving a request.

The above-described and other features and advantages of the present disclosure will be appreciated and understood by those skilled in the art from the following detailed description, drawings, and appended claims.

BRIEF DESCRIPTION OF THE DRAWINGS

A component or a feature that is common to more than one of FIGS. 1-18 is indicated with a same reference number in each of the drawings.

DESCRIPTION

Figure 1:
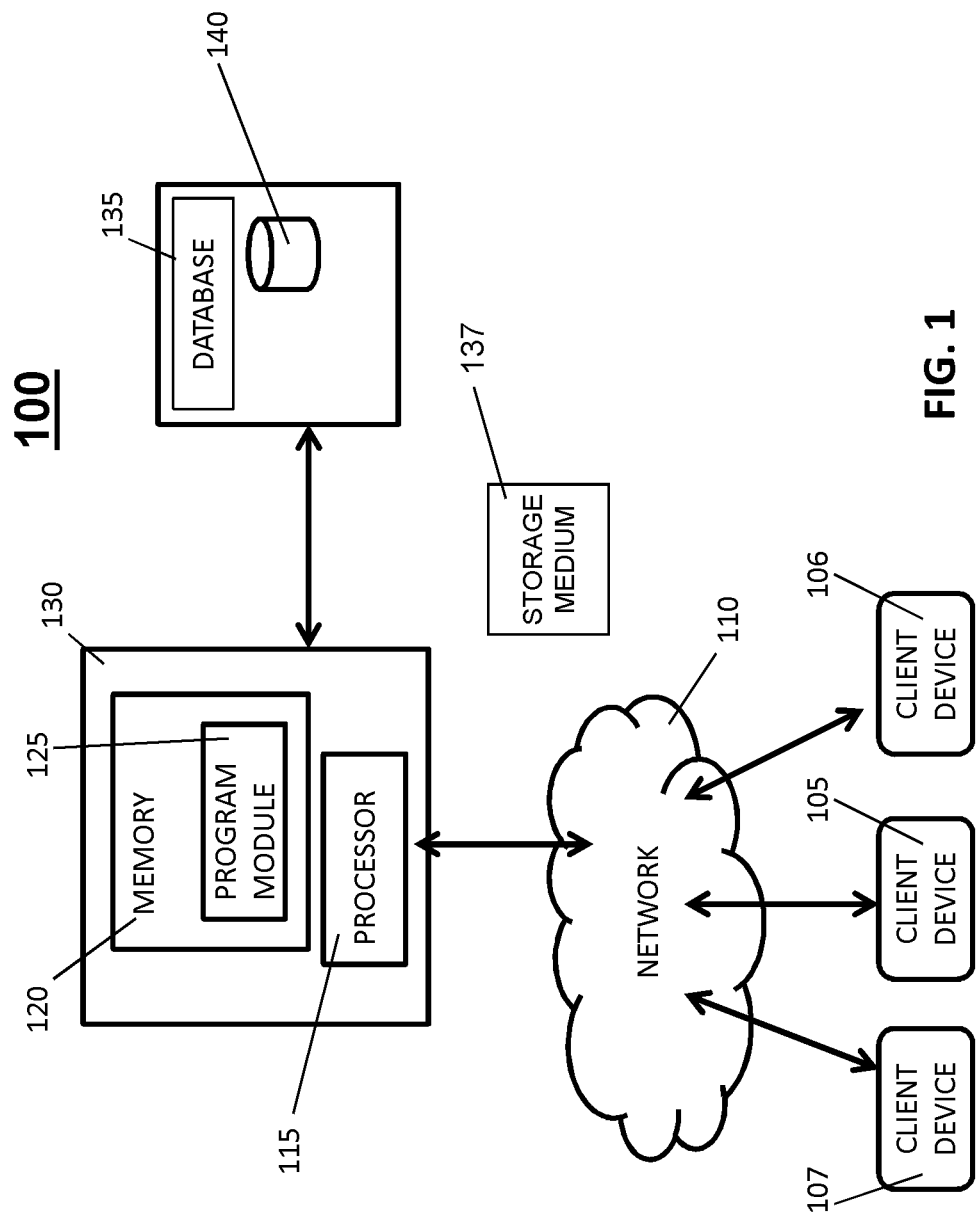
FIG. 1 illustrates a diagnostic system.

FIG. 1 illustrates a diagnostic system, e.g., system 100 according to the present disclosure. System 100 includes a client device 105, a network 110, a computer 130 and a database 135. Computer 130 includes a processor 115 and memory 120. Memory 120 further includes a program module 125 and database 135 includes a record 140.

Client device 105, 106 and 107 can be access devices, including, but not limited to: a computer, a personal computing device, a personal data assistant (PDA), a mobile phone, a keyboard, or a touch screen enabled device. Client device 105, 106 and 107 enables a user (not shown), e.g., a patient or a physician, to communicate information via network 110 to computer 130. Typically, Client device 105, 106 and 107 also include a means for display.

Processor 115 is an electronic device configured of logic circuitry that responds to and executes instructions.

Memory 120 is a computer-readable medium encoded with a computer program. In this regard, memory 120 stores data and instructions that are readable and executable by processor 115 for controlling the operation of processor 115. Memory 120 may be implemented in a random access memory (RAM), a hard drive, a read only memory (ROM), or a combination thereof. One of the components of memory 120 is program module 125.

Program module 125 contains instructions for controlling processor 115 to execute the methods described herein. The term "module", as used herein, denotes a functional operation that may be embodied either as a stand-alone component or as an integrated configuration of a plurality of sub-ordinate components. Thus, program module 125 may be implemented as a single module or as a plurality of modules that operate in cooperation with one another. Moreover, although program module 125 is described herein as being installed in memory 120, and therefore being implemented in software, it could be implemented in any of hardware (e.g., electronic circuitry), firmware, software, or a combination thereof.

While program module 125 is indicated as already loaded into memory 120, it may be configured on a storage medium 137 for subsequent loading into memory 120. Storage medium 137 is also a computer-readable medium encoded with a computer program, and can be any conventional storage medium that stores program module 125 thereon in tangible form. Examples of storage medium 137 include a floppy disk, a compact disk, a magnetic tape, a read only memory, an optical storage media, universal serial bus (USB) flash drive, a digital versatile disc, or a zip drive. Alternatively, storage medium 137 can be a random access memory, or other type of electronic storage, located on a remote storage system and coupled to computer 130 via network 110.

In operation, system 100 provides for creation of a record for a lesion, e.g., a skin lesion. The user, via client device 105, creates a record 140. Record 140 typically includes data such as, but not limited to: image data, lesion data, anatomical marker data, video data, specific descriptive terms, and audio data including a patient's own words to characterize the signs and symptoms of lesions and any related disease. skin type data, medical allergies data, current medications data, audio data, textual data and video data. Lesion data further includes descriptors of the lesion such as a color, a presence or absence of pain, a texture such as tense, fragile, firm, friable, Bleeding, Oozing, and Size. Record 140 is typically generated by client device 105. For example, data of record 140 such as image data is generated by a camera of client device 105. Accordingly, client device 105 allows the user to create image data of the lesion, e.g., taking a photograph using the camera. Client device 105 may also display a body map, e.g., an avatar of a digital representation of a human body. Preferably, the body map is anatomically correct and gender specific according to the user. The user selects a location on the body map that corresponds to the location of a site of the lesion on the user resulting in an anatomical marker. Client device 105 outputs the image and the anatomical marker to processor 115, via network 110. The image and the anatomical marker are received and processed by processor 115, thus yielding a record 140. In some embodiments, a plurality of records for an individual user are created and stored in database 135 according to a patient profile. As multiple records are created, the patient profile tracks a progression of the lesion, e.g., a birth of the lesion, an excisional biopsy, a diagnostic picture of the histology, scars at a site of treatment, and any signs of recurrence. Typically, the multiple records provide a series of images or a video progression of the lesion.

A physician, e.g., a dermatologist, via client device 106 and 107 may access the record, e.g., a first record, stored in database 135. For purposes of discussion a first record includes patient data. It is to be understood by those skilled in the art that the first record may be a plurality of records stored according to a patient profile. The physician further analyzes the first record and attaches physician data such as, but not limited to: a preliminary diagnosis, additional image data taken at a physician's office, a preliminary diagnosis, and any combination thereof. The physician data is attached to the first record and stored as a second record in database 135. In some embodiments the second record may be stored in additional databases (not shown). It is to be understood and appreciated by those skilled in the art that a plurality of databases may be used in conjunction with each other to provide seamless access patient and physician records, e.g., first and second records. For purposes of illustration FIG. 1 illustrates a single database, database 135. An additional physician, e.g., a dermatopathologist, accesses the additional record via client device 107. The dermatopathologist renders a diagnosis based upon the additional record, thus yielding a third record. The third record is stored in database 135 and is accessible by client device 105 and client device 106.

Program module 125 can also contain instructions that cause processor 115 to issue an alert to the patient. The alert may be a reminder to create an additional record at specific time intervals. Creating additional records at specific time intervals facilitates an accurate and efficient evaluation of the progression of the lesion. The record and the additional records provide a rich source of previously unavailable sequential images of a same lesion for an individual user during a natural history of the lesion and the disease. This, in part, provides a basis on which a clinical and a pathological (and definitive) diagnosis of many lesions can be made or supported. Small progressive changes in the lesion can be discerned from an analysis of a series of images of the same lesion by reference to the anatomic landmarks. The series of images may be stored as individual records according to a client profile.

Program module 125 can also contain instructions that cause processor 115 to create a frame that provides an optimal alignment of an image area prior to the image being generated. Typically, the frame is superimposed in the image area prior to an image being taken. The frame may include, but is not limited to: an anatomical landmark, a ruler, a ruler-scale, or other measurement indicator. The anatomical landmark varies according to a user. For example, some anatomical landmarks may include, but are not limited to: a freckle, a scar, an end of a limb, a joint, or a non-lesion skin discoloration. The anatomical landmark is identified from a transparent image due to a color-contrast of the anatomical landmark against the background skin. Processor 115 superimposes the transparent image having the anatomical landmark as a frame in the image area. That is, a client device 105 may have a camera and a preview display. The preview display allows the user to preview the image area prior to taking an image. Processor 115 may superimpose the anatomical landmarks via the transparent image in the preview display to ensure the optimal alignment of the image area prior to the image being generated. Accordingly, images taken with the frame superimposed allow the anatomic landmarks to be used as a reference point. The reference point allows subtle changes in the lesion to be compared and assessed against throughout the series of images. Additionally, the frame facilitates a border detection method to calculate a lesion dimensions. Further, a rate of progression may be calculated as a function of the changing lesion dimension over time. In other embodiments, the frame is a ruler scale, or the like, and measures a focal point of the lesion.

System 100 provides an effective way to store records that chart an entire sequence of a lesion and an associated disease from the "birth" of the lesion, an evolution up to the point of an excisional biopsy (necessary for a definitive pathological diagnosis, usually performed after a presumptive clinical diagnosis is made; and which removes and sometimes cures the disease) to the diagnostic histological pictures and then to the final pictures of the scar at the site of treatment, as well as any sign of recurrence. This sequence, from birth to end to recurrence, represents a valuable training tool for clinicians and pathologists, while giving patients that are so inclined an opportunity to participate in their own skin care and to contribute to the body of knowledge used to train doctors and other clinicians as well as scientist and cosmetologists in medicine, research and esthiology.

System 100 further allows a patient to interact with a clinician and pathologist, and in so doing allows the patient to participate in the decision about where and to whom biopsies of the patient's lesion are sent. For example, a pathologist may elect to transmit a self addressed express mailing label to a patient or a dermatologist along with the label for the specimen container. The label may be printed directly from a networked local printer (in communication with client device 105). In this fashion, the specimen container can be easily shipped to the dermatopathologist in a distant location using overnight shipping service.

System 100 still further allows a dermatopathologist to be available and to communicate directly with the patient and with the dermatologist and to offer a more patient-oriented service. Thus, the dermatopathologist in effect becomes a clinician-pathologist due to his proximity to the patient and dermatologist through this network of devices. System 100 also advantageously enables practitioners, pharmaceutical companies and other related health care service providers to offer directed targeting of services to patients with specific needs/diseases.

System 100 still further facilitates remote monitoring of a patient's collected data by computer algorithms and medical practitioners. Thus, system 100 advantageously provides a basis for advising and communicating with patients at a distance through multimedia systems. When appropriate a patient receives a signal with advice to self medicate, collect additional information or to communicate with or seek medical attention from a practitioner.

Figure 2:
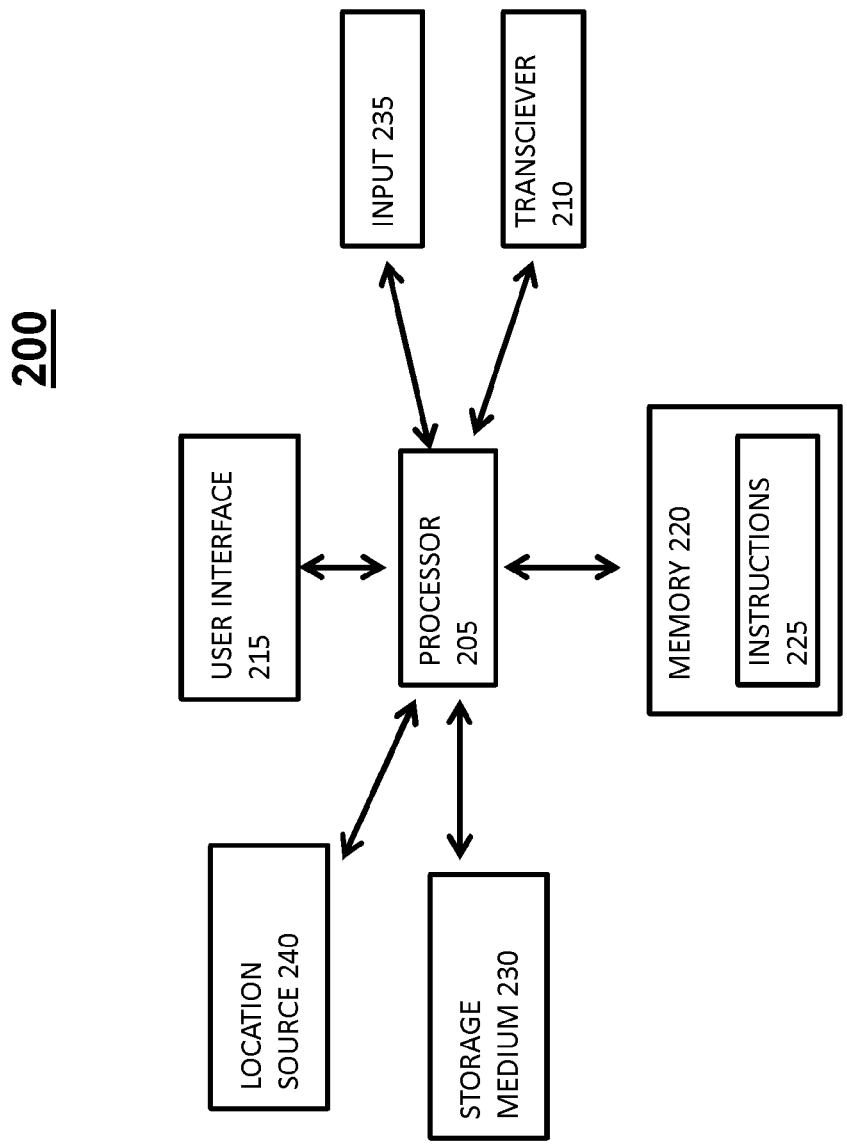
FIG. 2 illustrates a diagnostic client system.

FIG. 2 illustrates a diagnostic client system, e.g., system 200. System 200 provides a central processor 205 in communication with a plurality of modules. As used herein, the term "module" may denote a functional unit that is implemented in one or more of software, firmware, hardware, and equivalents thereof.

One such module is a transceiver 210. Transceiver 210 is a device that interfaces to a communication network including, but not limited to: a mobile telephony network, a TCP/IP network, and a circuit-switched network.

System 200 also includes a user interface 215. User interface 215 provides an input (not shown) that is a man-machine interface (MMI) with controls for a user to command system 200. User interface 215 further provides an output (not shown) for communicating prompts, alerts, menus, dialogs, and other signals that are perceptible to a user. In a preferred embodiment, user interface 215 supports a tactile and graphical user environment.

System 200 further provides a memory 220 that is in communication with processor 205. Memory 220 includes instructions 225 for execution by processor 205. Instructions 225 are persistently stored on a storage medium 230 for loading into memory 220 to cause processor 205 to carry out the steps of methods described herein. Examples of storage medium 230 include a floppy disk, a compact disk, a magnetic tape, a read only memory, an optical storage media, universal serial bus (USB) flash drive, a digital versatile disc, or a zip drive. Storage medium 230 can be a random access memory, or other type of electronic storage, located on a remote storage system. Storage medium 230 may be physically distant, e.g., remote, to processor 205, local to processor 205, or some combination of local and remote.

System 200 also provides a location source 240. Location source 240 is in communication with processor 205 and provides location data for system 200. In one embodiment, location source 240 is a GPS receiver, however, it is to be understood and appreciated by those skilled in the art that location source 240 may be any remote geo-coding service, or even a manually-entered location.

Processor 205 is also in communication with an input 235 that provides data such as data of record 140. In an embodiment, input 235 is an image or video input. However, it is within the contemplation of the present disclosure that input 235 may be any suitable input that is capable of assaying a patient and outputting a machine-readable output; by way of example, a scale, a sphygmomanometer, a spirometer, thermometer, pulse oximeter, pacemaker, ion-specific electrodes, microphone, and the like.

Figure 3:
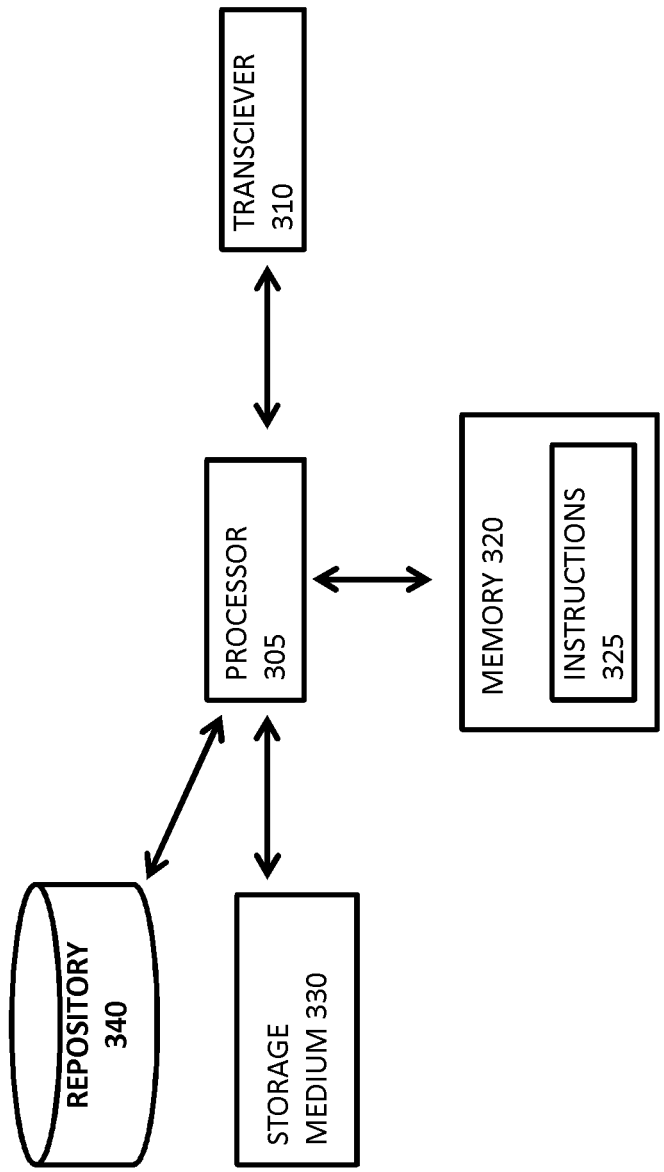
FIG. 3 illustrates a diagnostic client system.

FIG. 3 illustrates a diagnostic database system, e.g., system 300. System 300 provides a processor 305 that is in communication with a plurality of modules.

One such module is a transceiver 310. Transceiver 310 interfaces with a communication network such as, for example, a mobile telephony network, a TCP/IP network, or a circuit-switched network. System 300, via transceiver 310, is in communication with one or more diagnostic client devices (not shown) over the communication network.

System 300 further provides a memory 320 in communication with processor 305. Machine-readable instructions 325 are resident in memory 320 for execution by processor 305 to cause processor 305 to carry out the steps of methods described herein. Instructions 325 are stored on a storage medium 330 for loading into memory 320. Storage medium 330 in turn may be physically distant to processor 305, local to processor 305, or some combination of local and distant.

Processor 305 is further in communication with a database 340 for storing a record, e.g., record 140. It is to be understood that multiple records may be stored in database 340. The record may include data of record 140 described above or, alternatively the record may include physician data. For example, the record may include physician data such as treatment data, location data and a physician's experience data. A physician's experience data may include data such as publication data, workshop data, community lectures data, and historical diagnosis data. The location data is a location of a physician or a physician's office and includes a latitude/longitude (lat/lon) coordinate. In this fashion, a potential patient may access the record in database 340 via transceiver 310 and processor 305 to obtain the location of nearby physicians or nearby physicians' offices. This assists the potential patient locate local treatment options, e.g., local physicians that can assist in treatment of the skin lesions. Alternatively, a potential patient, via client device 105, may access physician data to select a physician based upon experience data.

Figure 4:
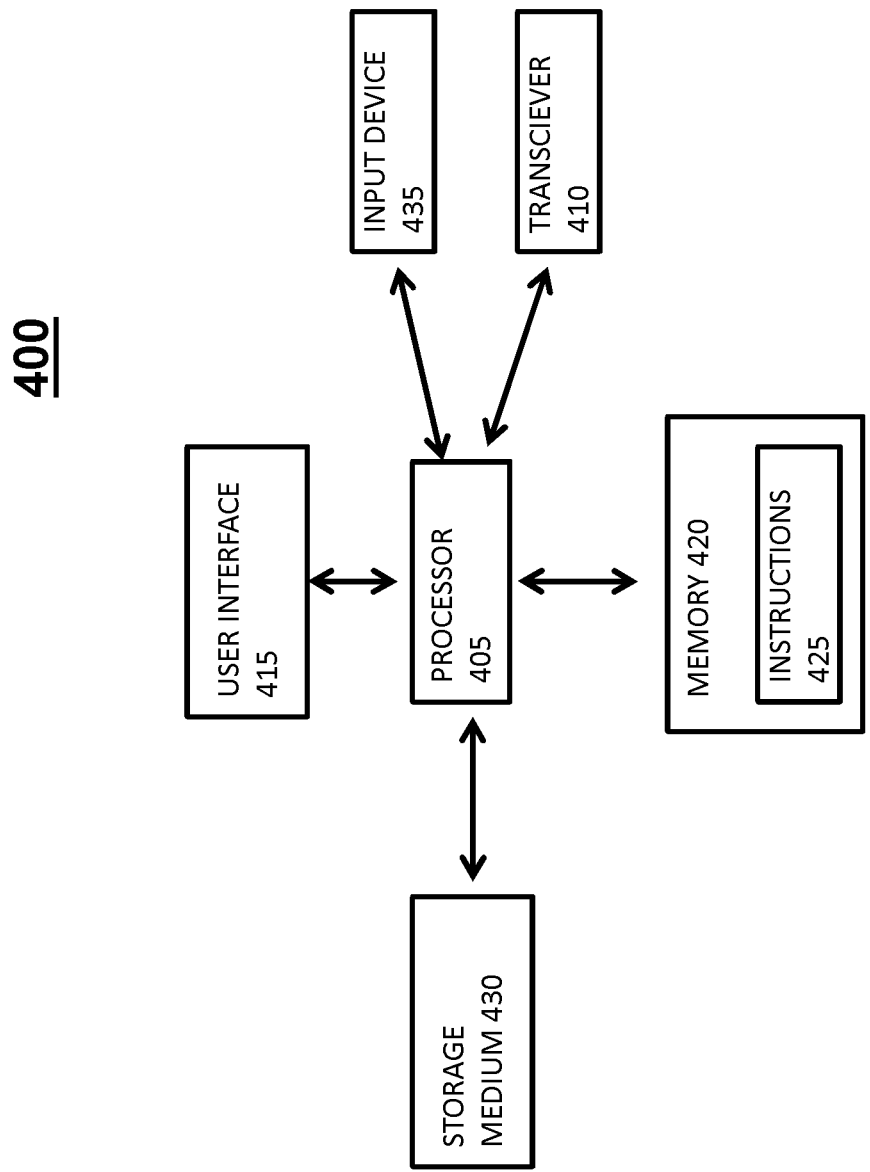
FIG. 4 illustrates diagnostic client system.

FIG. 4 illustrates a diagnostic client system, e.g., system 400. System 400 provides a central processor 405 that is in communication with a plurality of modules.

One such module is a transceiver 410. Transceiver 410 is an interface to a communication network such as, for example, a mobile telephony network, a TCP/IP network, a circuit-switched network, or the like.

A further such module is a user interface 415. User interface 415 provides an input that is a man-machine interface (MMI) with controls for a user to command system 400. User interface 415 further provides an output (not shown) for communicating prompts, alerts, menus, dialogs, and other signals that are perceptible to the user. In a preferred embodiment, user interface 415 supports a tactile and graphical user environment.

System 400 further provides a memory 420 that is in communication with processor 405. Machine-readable instructions 425 are resident in memory 420 for execution by processor 405. Instructions 425 are stored on a storage medium 430 for loading into memory 320 to cause processor 305 to carry out the steps of methods described herein. Storage medium 430 in turn may be physically distant to processor 405, local to processor 405, or some combination of local and distant.

Processor 405 is also in communication with an input device 435 that inputs data such as patient data and physician data. The input data includes, but is not limited to: pictures, images and video. It is within the contemplation of the present disclosure that input device 435 may also be any suitable input device capable of assaying a patient and a machine-readable data. For example, an input device may include, but is not limited to: a scale, a sphygmomanometer, a spirometer and a photo-taking microscope.

Figure 5:
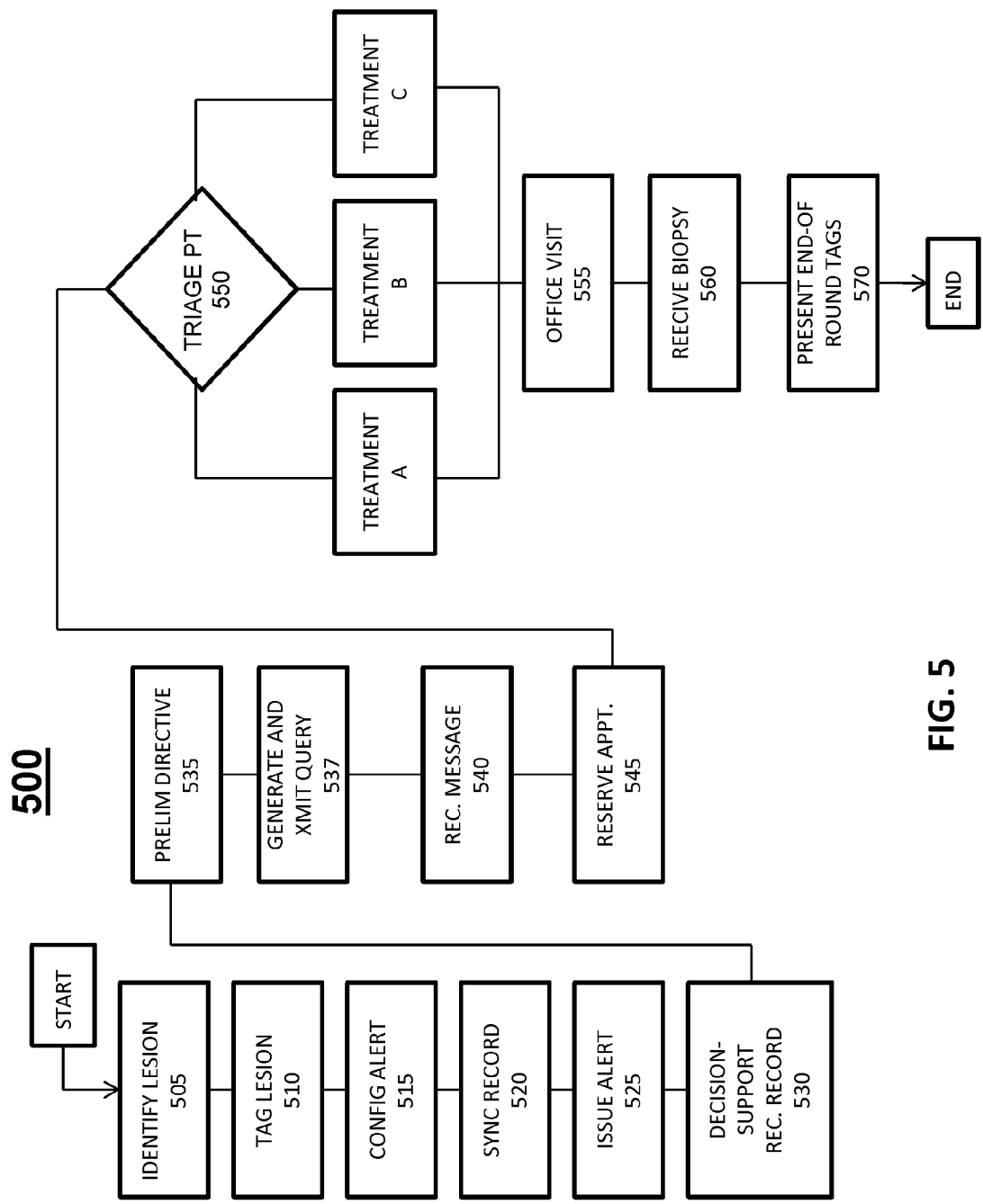
FIG. 5 is a method illustrating a lifecycle of a medical diagnosis and a treatment.

FIG. 5 is a method illustrating a lifecycle of a medical diagnosis and a treatment, e.g., method 500. Method 500 is executed with reference to system 200 of FIG. 2 and system 300 of FIG. 3.

FIG. 5 begins at step 505, identifying a lesion. Next, at step 510, the lesion is tagged, e.g., "tag lesion". As used herein, the word "tag" means creating a record for the lesion. The record is typically in a digital format and includes data such as, but not limited to: physical properties of the lesion, a location of the lesion on a body of a patient; patient comments about the lesion, e.g., a chief complaint, a time of record creation, and image data of the lesion. In one embodiment, the physical properties of the lesion are measured by input device 435. Alternatively, the physical properties may be described and incorporated into the record by a physician. The record is accessible in real-time. That is, once the record is created, a patient or physician may access and analyze the data. Analysis of the data in real-time improves diagnosis and treatment of the lesion and allows a physician to issue instructions pertinent to a present condition such as requesting additional images from the patient and schedule a follow-up appointment.

At step 515, an alert is configured. For example, system 200 may be configured to display the alert to the patient via user interface 215. The alert is a reminder to the patient and can be configured to issue after a time t has elapsed or at the command of another user, e.g., a physician. The alert may contain information such as instructions for the patient to tag the lesion again, e.g., create another record for the lesion. For example, the alert may be configured to issue to user interface 215 if a prior record contained data containing a blurred image. Alternatively, the alert could be configured according to a schedule for repeatedly creating records of the lesion at specified periods of time. In this fashion, a progression of the lesion and an associated disease causing the lesion may be documented as a series of records.

At step 520, method 500 synchronizes the record. For example, a patient using system 200 may create a record saved to storage medium 230. The patient uses user interface 215 to indicate the record is in a condition to be synchronized with database 200 and the record is then synchronized, e.g., uploaded. The record is transmitted by transceiver 210 and received by transceiver 310 of system 300. System 300, in turn, stores the record in database 340.

At step 525, an alert is issued, e.g., communicated, to system 200 causing a display of the alert configured in step 415. Client 100 typically displays the alert configured in step 415.

At step 530, a user, e.g., a decision-support physician receives the record from system 300 and performs a medical analysis of data within the record as well as any metadata generated. In one embodiment, system 300 also transmits decision-support data that is generated from the record. The decision-support physician in turn categorizes the record according to a lesion type, and causes system 300 to transmit a message to the patient. The message may include, but is not limited to: a request for information, feedback, and a preliminary treatment directive. The preliminary treatment directive may include information that advises the patient to seek a physician, e.g., "seek a treating dermatologist and dermatopathologist". If step 530 yields a preliminary treatment directive, method 500 provides step 435.

At step 535 the patient receives the preliminary treatment directive. After receiving the preliminary treatment directive, the patient at step 537 creates a query that identifies a treating physician and a dermotopathologist within a specified area, e.g., a specified distance d from the patient. For example, the patient may use system 200 to find a treating physician and a dermotopathologist located within a patient-configurable distance. The patient-configurable distance may be derived from location source 240 of system 200. The query is transmitted from system 200 and received by system 300.

At step 540, system 300 receives a message in response to the query. The message is transmitted from system 200 and received at system 300. Preferably, the message includes a list of treating physicians and dermatopathologists located within distance d. The message can also include, but is not limited to: various promotional and certification information for each physicians and dermatopathologists, as well as available times for office visits, verbal consultation, video consultation, telephone conferencing and combinations thereof. The patient selects an available time with a treating physician of the patient's choosing or the patient requests a specific pathologist to review his or her biopsy, based on a profile of previous service, diagnose, academic papers on related subjects or general interest. In alternative embodiments, the message may be a physician record. Typically, the physician record include information described-above for the message, however, the physician record may further include publication data, workshop data, community lectures data, historical diagnosis data, and combinations thereof.

At step 545, the patient reserves an available time for an office visit with a reservation message. The reservation message includes the record created at step 505. The reservation message is transmitted to the treating physician.

At step 550, the treating physician triages the patient based on the record and prescribes a first round of treatment for the patient accordingly.

At step 555, the patient is seen in person by the treating physician, and the treating physician generates professional-quality data and appends the professional-quality data to the record. For instance, the treating physician adds formal dermatologic imaging of the patient's lesion to the record. The treating physician may also communicate with a dermatologist regarding a possible biopsy of the lesion for further analysis.

At step 560, the dermatopathologist receives the biopsy, and the record. The dermatopathologist, in turn, performs further analysis as well as photomicrography of the biopsy as part of his interpretation of the findings and rendering of a diagnosis. The photomicrographic images and the diagnosis and other descriptions are added to the record, which data are synchronized with database 200 analogously with step 420 to produce end-of-round tag data.

At step 570, system 200 obtains end-of-round tag data, which data are presented to the patient on user interface 215. The patient is thus able to view his tag data (see step 405), the treating physicians additions to the tag data, as well as those of the dermatopathologist.

Figure 6:
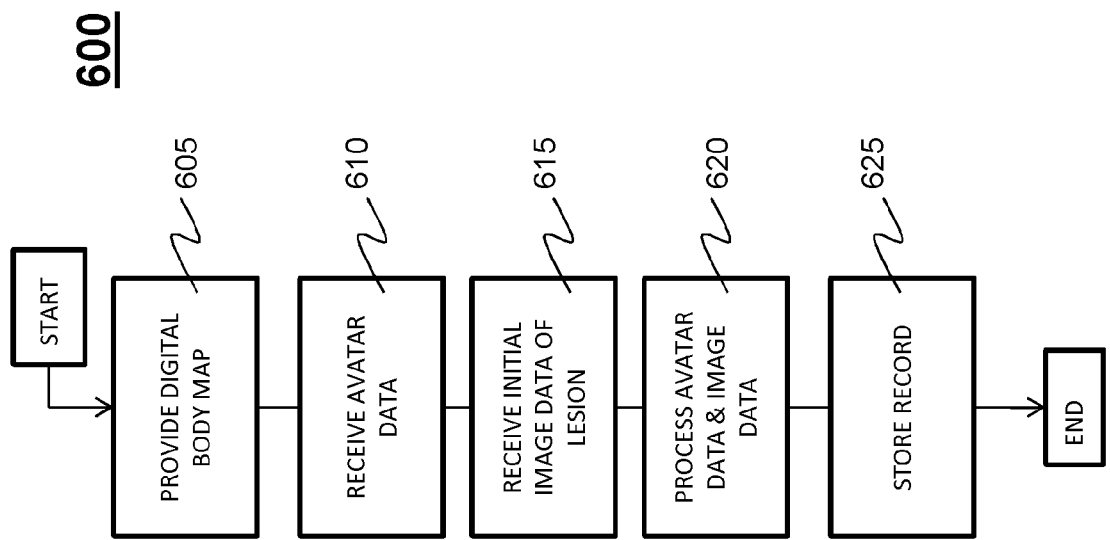
FIG. 6 is a method for cutaneous diagnosis.

FIG. 6 is a method for cutaneous diagnosis, e.g., method 600. Method 600 begins at step 605 and requires providing a digital body map. Next, at step 610, receive avatar data. The avatar data includes an anatomical marker associated with a location of a lesion on the digital body map. At step 615, receive initial image data of the lesion. Next, at step 620, process the avatar data and the image data yielding patient data. Finally, at step 625, store the patient data and the avatar data as a first record in a database. Thereafter, method 600 ends with END. In additional embodiments, method 600 further includes receive additional image data, process the avatar data and the additional image data yielding a second record, process the first record and the second record yielding a patient profile, store the patient profile in a database, receive a request for the patient profile, and finally provide the patient profile as a result of receiving the request.

Figure 7:
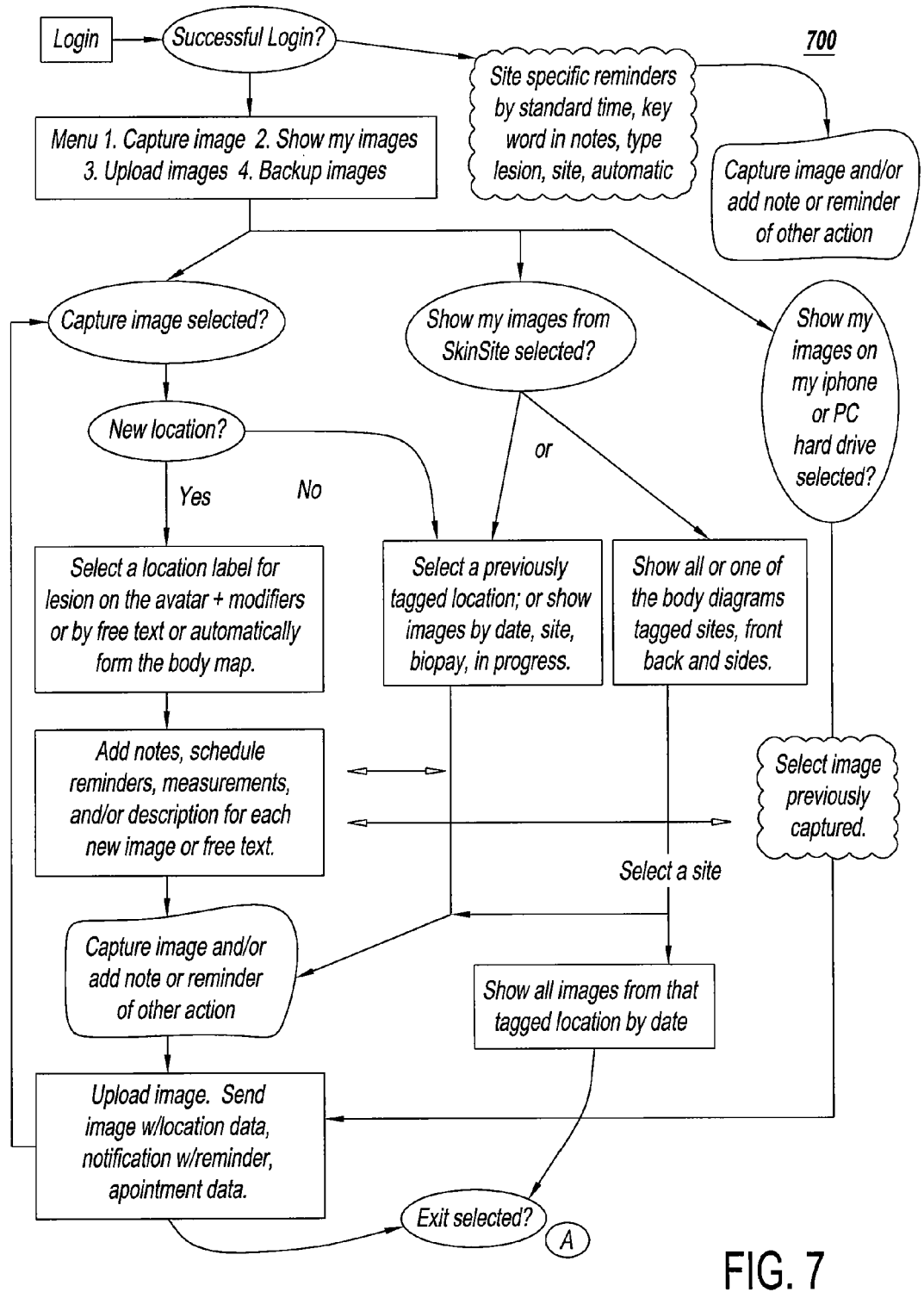
FIG. 7 is a component flow diagram for a client-database system.

FIG. 7 is a component flow diagram, e.g., diagram 700, for a client-database system according to an embodiment of the present disclosure. Here a patient logs in and is able to capture images data, review prior image data, review alerts, e.g., reminders, for new image data to be captured, save the new image data with annotation, and share the new image data with the clinicians of his/her choice, by synchronizing the application with a database.

Figure 8:
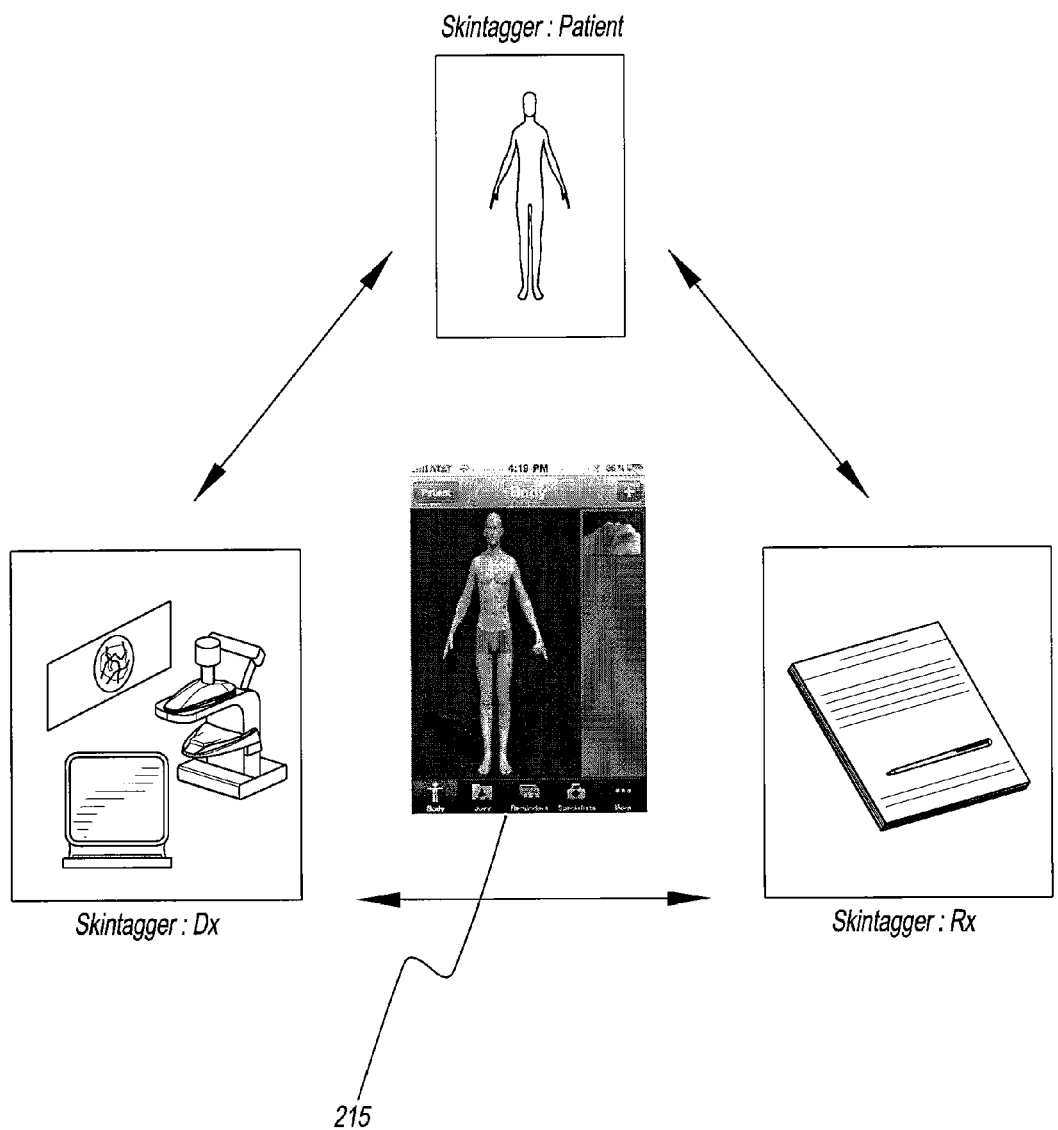
FIGS. 8-18 show a user interface of a client system according to the present disclosure.

FIGS. 8-18 are views of a user interface of systems in accordance with an embodiment of the present disclosure. The user captures, annotates and shares image data with clinicians who may communicate among themselves or with the patient to obtain the most complete information from the patient for the synthesis of the diagnosis. Additional information from a disease knowledge database, the location of the clinicians, as well as their schedules and availability can be integrated into the application to facilitate expeditious management of the lesion, the biopsy and the treatment by the patients and clinician. For example, FIG. 8 shows user interface 215 that is displaying to a user a digital body map, e.g., an avatar, in the shape of person representing a patient. The avatar has a plurality of anatomical markers displayed thereon, which anatomical markers correspond to a plurality of disease sites of the patient. A right-hand side of user interface 215 shows clinical and cytology/histology images that pertain to the plurality of disease sites, each image displayed represents the most recent in a series of images from a corresponding site tagged by colored dots on the body map. Indicia on the dots or changes in color of the dots represent information about the disease site sent among the users (including the clinicians or patient).

In addition, FIG. 8 illustrates a relationship between different parties. For example, a patient, at home, may notice a lesion such as a rash or a tumor on his/her skin or other body site. The patient may use a client device (not shown), e.g., a smart phone, to capture a picture, audio or text to document the lesion over a period of time, e.g., days or weeks. The patient can synchronize the documented data with a participating clinician and dermatopathologists for remote evaluation. The patient can receive feedback from the clinician or dermatopathologists, including, but not limited to: a remote clinical assessment and prognosis, an available appointment time for a live assessment, directions to an office and other information about the clinician and practice. In addition, the dermatopathogist may have a more sophisticated version of software with an option to give access to an office schedule, an interface to a knowledge database for skin diseases, e.g., database 135. Follow up appointment and additional surgeries can be monitored by dermatopathologists using the more sophisticated software. Further, the dermatopathologist can be notified that a new biopsy has been performed by a dermatologist on the patient's body site. The dermatologist may further provide a clinical history and a chief complaint, accessible directly from the dermatologist and the patient. Clinicopathologic correlation may be performed and include the patient directly. This diagnosis can be correlated with patient data and synchronized amongst all parties, e.g., patient, dermatologist, dermatopathologists.

Figure 9:
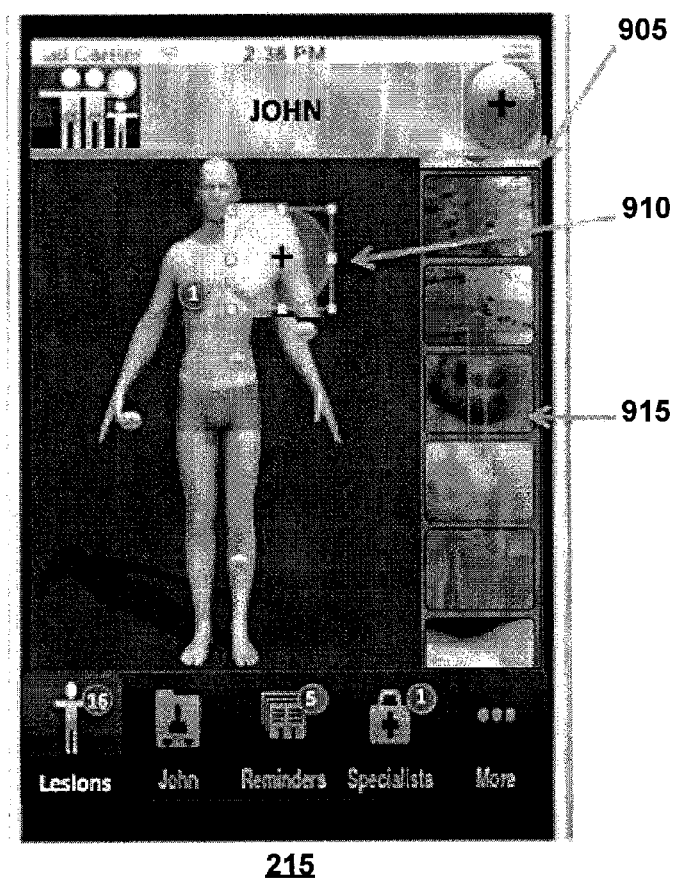

FIG. 9 shows user interface 215 that is displaying to a user an avatar representing a patient. User interface 215 provides functionality for zooming in on and adjusting a view of the digital body map, for selecting representations of markers on the digital body map, and for scrolling through medical imagery relating to the patient represented by the digital body map.

In particular, FIG. 9 illustrates how a patient may tap a picture in a vertical carousel 905 on the left hand side for a close-up view of a prior taken image, i.e., image 915. This carousel may provide scrolling to access all the images previously stored. Further, FIG. 9 illustrates a one touch tagging. That is, a patient may tap a body part to call up a magnifying glass 910 that includes a plus sign. Tapping the plus sign may signal to the client device to enable a camera to take a image of lesion at a particular location.

Figure 10:
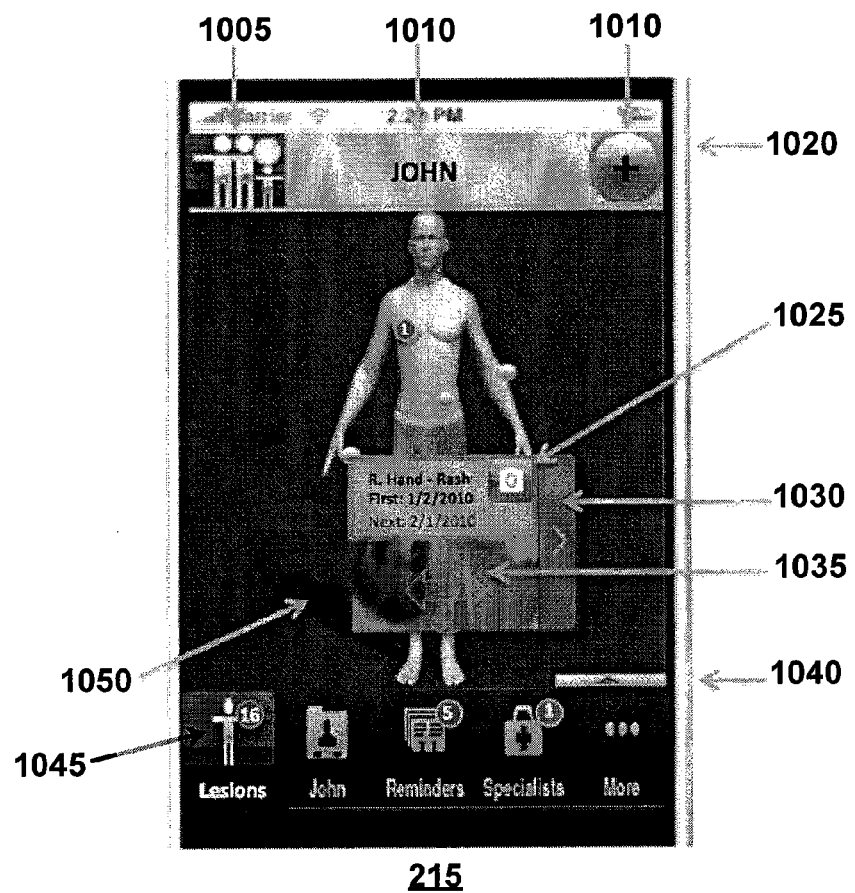

FIG. 10 shows user interface 215 that is displaying an avatar and a prompt for accessing a detailed view of a disease site on the digital body map. A lower edge of user interface 215 presents prompts for accessing reminders, and for accessing a geographically-based list of medical practitioners.

In addition, FIG. 10 displays additional functionality displayed on user interface 215. User interface 215 provides a feature 1005 that displays all patients in a system and, additionally, provides reminder notices. Feature 1010 displays a name of an active patient. Feature 1015 allows additional data such as an image, notes, or a reminder, to be added to a record. Feature 1020 is a touch option that provides a magnifying glass with cross hairs that allows an additional image and location to be tagged. Feature 1025 allows additional images to be added to a series at a particular location of a lesion. Feature 1030 displays lesion site detail or image detail. Feature 1035 provides additional details of an image. A double tap illustrates a full screen image. Feature 1040 allows all lesion sites, e.g., a lesion image and a lesion location, to be displayed. Feature 1045 is a lower menu that displays (from left to right) a home body, information on a patient, reminders, doctor communication and medical appointments, public health information, medical information, video demo of application, and application preferences. The home body includes all information in a summary form and access to all information details with one touch (if possible). Feature 1050 allows a user to swipe through all images at a particular lesion site. Tapping feature 1050 shows a full screen image.

Figure 11:
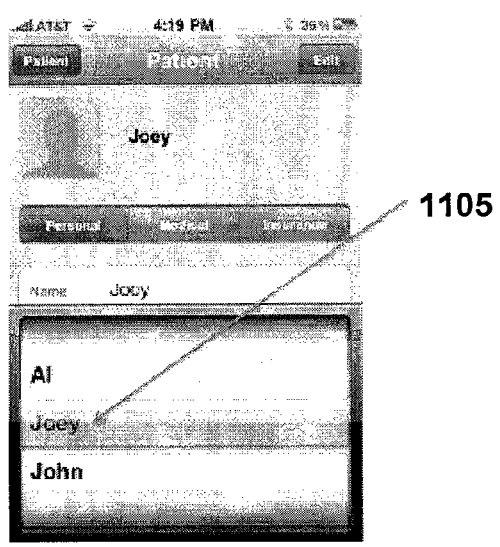

FIG. 11 shows user interface 215 in patient selection mode. A user is presented with a list of patients 1105 by name for selection.

Figure 12:
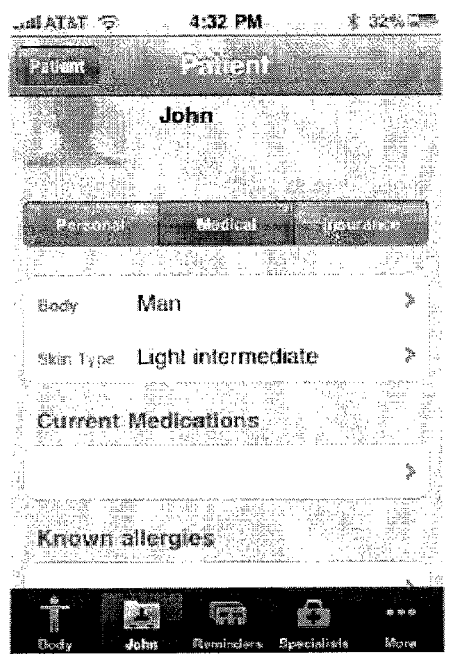

FIG. 12 shows user interface 215 in patient information mode. A user is presented with dialogs for assigning and displaying information of a patient, such as skin type, known medical allergies, and medications being taken by the patient.

Figure 13:
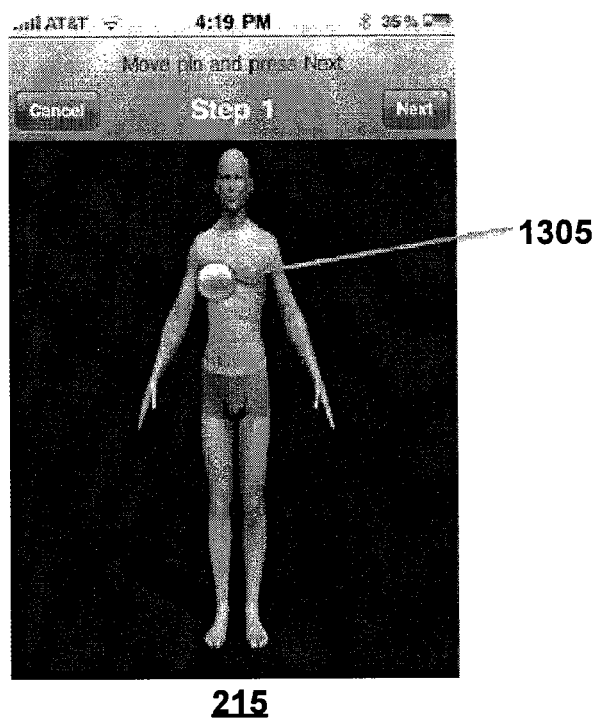

FIG. 13 shows user interface 215 in a marker adding mode. A user moves a pin-like marker 1305 over a location on an avatar in order to indicate a physical location of a disease site such as a skin lesion.

Figure 14:
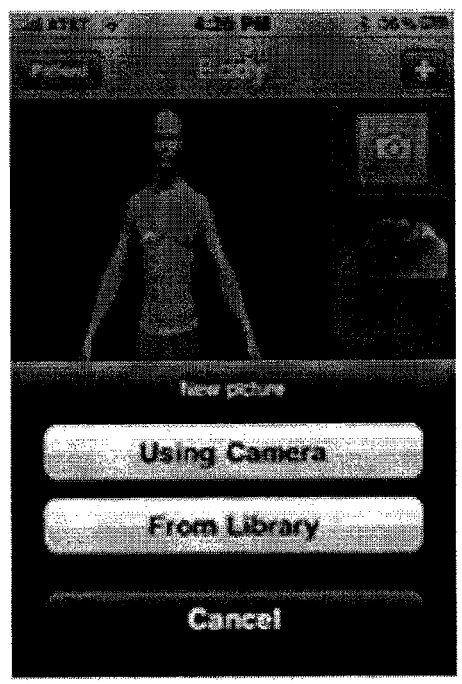

FIG. 14 shows user interface 215 in a photo-adding mode. A user is prompted to select a photo source. The photo source can be, for example, a camera that is in communication with system 200 (or system 300) or can be a so-called library of images. In an embodiment of the present disclosure, the library is stored in database 340.

Figure 15:
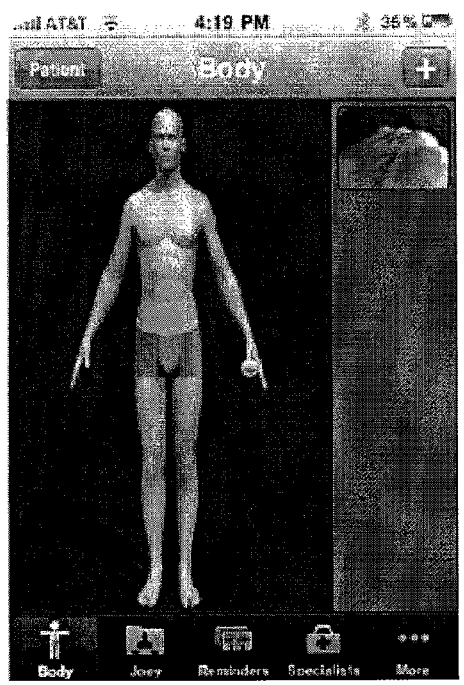

FIG. 15 shows user interface 215 in tag-and-photo-adding mode. A user is presented with imagery data for a lesion site. When the user selects a particular imagery datum, an indicia on the displayed avatar is highlighted (as by vibrating on user interface 215, by changing color or other attention-commanding methods).

In addition, the body avatar of user interface 215 may rotate when the user swipes a finger on the body avatar.

Figure 16:
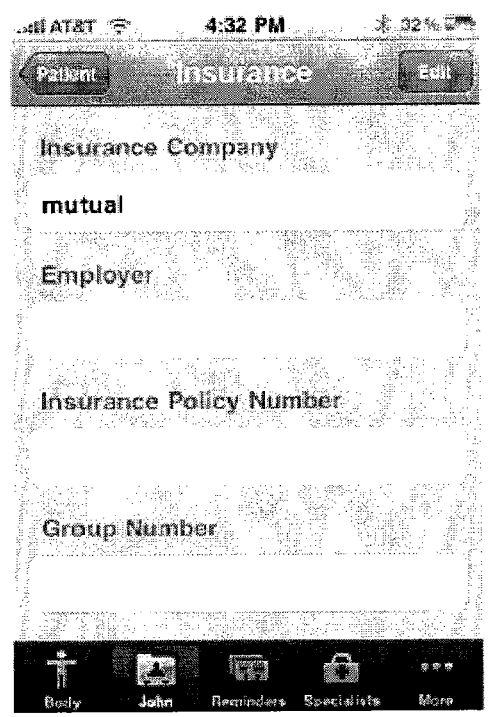

FIG. 16 shows user interface 215 in insurance information mode. A user is prompted to enter (or may view pre-existing) data pertaining to a patient's health insurance records.

Figure 17:
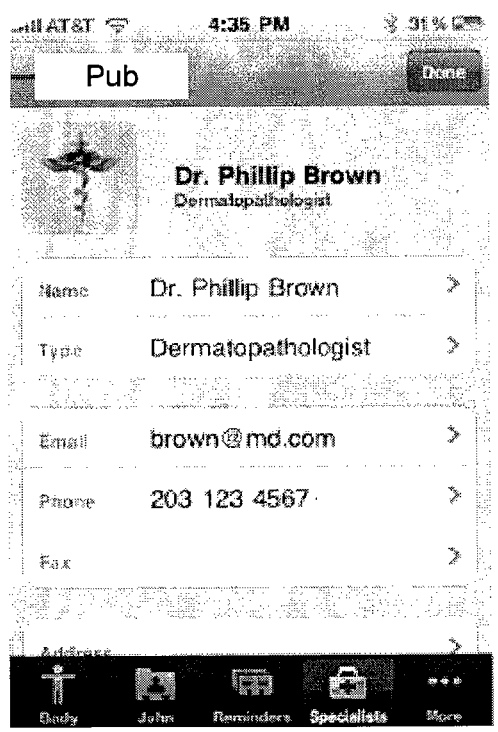

FIG. 17 shows user interface 215 in physician-access mode. A record pertaining to a medical practitioner is presented to the user. The record comprises information such as publications, qualifications, and contact information for the medical practitioner. In an embodiment, the user is presented with a record according to one or more of the user's and the practitioner's geographic location.

Figure 18:
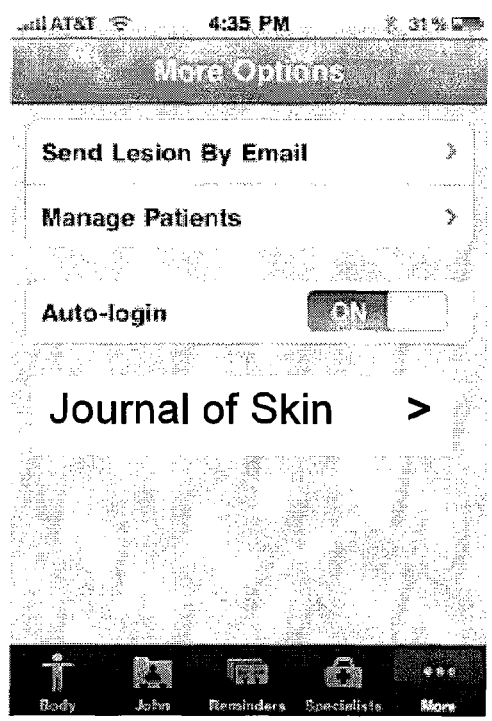

FIG. 18 shows user interface 215 in settings mode. In settings mode, the user is prompted to supply a destination for record data. For example, record data might be sent to a medical journal dealing with dermatology, for record data pertaining to a skin injury. The user also sets global functions within the application, such as storing credentials for automatic login into the application.

Figure 19:
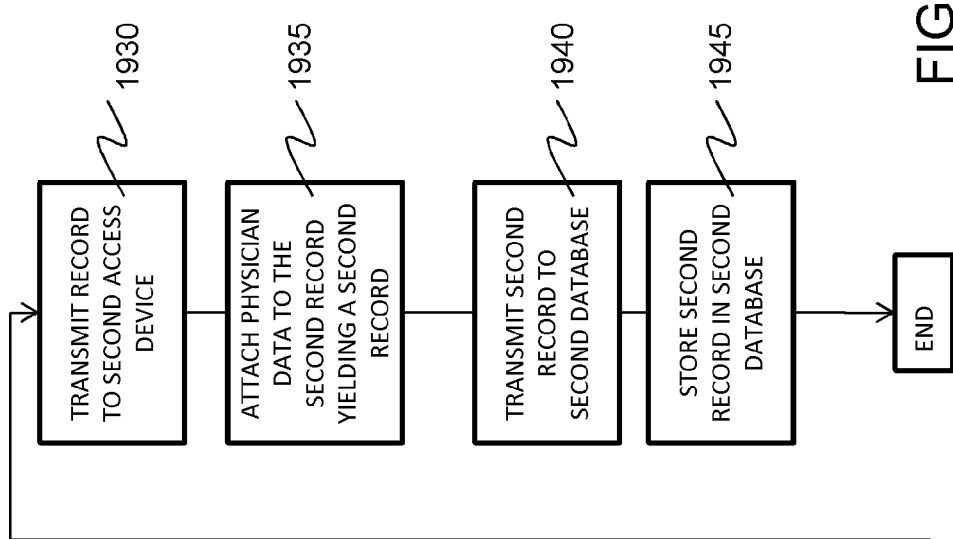
FIG. 19 is a method for cutaneous diagnosis.

FIG. 19 illustrates a method for cutaneous diagnosis, e.g., method 1900.

At step 1905 a lesion is imaged with a first access device.

At step 1910 the first access device displays a digital body map having an anatomical marker.

At step 1915, the anatomical marker and the image data are associated to yield a first record.

At step 1920, the first record is transmitted from the first access device to a database.

At step 1925, the first record is stored in the database.

At step 1930, the first record is transmitted from the database to a second access device.

At step 1935, physician data is attached to the first record via the second device, thus yielding a second record.

At step 1940, the second record is transmitted to a second database.

At step 1945, the second record is stored in the second database.

From step 1945, method 1900 ends.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A system for cutaneous diagnosis comprising:
a first access device of a patient, said first access device comprising a camera, a processor, and a display of a digital body map, wherein said camera captures at least a first image of a lesion, wherein a patient selection of a location on said digital body map that corresponds to a site of said lesion results in an anatomical marker, and wherein said processor tags said location of the lesion captured from said camera with said anatomical marker, thus yielding a first record;
a first database in communication with said first access device via a network, wherein said first record is transmitted by said first access device via said network to said first database and said first database receives and stores said first record;
a second access device of a physician in communication with said first database, said second access device retrieves said first record from said first database via said network and attaches physician data to said first record, said physician data comprises at least a second image of said lesion taken at said physician's office and at least one selected from the group consisting of: a preliminary diagnosis, and a preliminary treatment directive data, thus yielding a second record that is transmitted via said network to a second database and stored; and
a third access device of said dermatopathologist in communication with said second database, said third access device retrieves said second record from said second database via said network and attaches dermatopathologist data to said second record, said dermatopathologist data comprises a third image of a photomicrography of a biopsy of said lesion and a diagnosis based upon said first and second records, as well as a biopsy of said lesion, thus yielding a third record that is transmitted via said network to a third database and stored;
wherein said third record is accessible by said first and second access devices.

2. The system according to claim 1, wherein said first database, said second database, and said third database are a single database.

3. The system according to claim 1, wherein said third record is transmitted to at least to said first access device and/or said second access device.

4. The system according to claim 1, wherein said second record is transmitted from said second database via said network to said first access device.

5. The system according to claim 1, wherein said processor generates a frame from said image data, said frame is superimposed on said first access device to align subsequent image data, said frame comprises transparent image data having anatomical landmarks.

6. The system according to claim 1, wherein said first access device, said second access device and said third access device are at least one selected from the group consisting of: a PDA device, a computer device, a mobile-phone device, and a personal computing device.

7. A computer implemented method for cutaneous diagnosis comprising:
imaging a lesion with a first access device of a patient to form a first image data;
displaying a digital body map having an anatomical marker to said first access device;
associating said anatomical marker with said first image data of said lesion, thus yielding a first record;
transmitting said first record from said first access device via a computer network to a first database;
storing said first record in said first database;
transmitting said first record from said first database to a second access device of a physician;
attaching said physician data to said first record via said second access device, thus yielding a second record, wherein said physician data comprises at least a second image data of said lesion taken at said physician's office and at least one selected from the group consisting of: a preliminary diagnosis, and a preliminary treatment directive data;
transmitting said second record to a second database;
storing said second record in said second database;
with a third access device of said dermatopathologist in communication with said second database, retrieving said second record from said second database via said computer network; and attaching dermatopathologist data to said second record, said dermatopathologist data comprises a third image data of a photomicrography of a biopsy of said lesion and a diagnosis based upon said first and second records, as well as a biopsy of said lesion, thus yielding a third record that is transmitted via said computer network to a third database and stored, and wherein said third record is accessible by said first and second access devices.

8. The method according to claim 7, wherein said first access device has a specified area of interest, further comprising:

storing a physician record in said first database, said physician record comprising a name and a location of a physician; and retrieving, when said physician record is within said specified area of interest, said physician record for said first access device from said first database via said computer network.

9. The method according to claim 7, wherein said first database and said second database are a single database, the method further comprising:

storing a physician record in said single database, wherein said physician record comprises data selected from the group consisting of: promotional data, experience data, certification data, and any combination thereof;

accessing said physician record with said first access device; and selecting a physician based on said physician record.

10. The method according to claim 7, further comprising:

storing a physician record in said first database, wherein said physician record comprises schedule data of times for a physician consultation;

accessing said physician record with said first access device; and selecting a time for a physician consultation via said first access device, thereby generating an appointment.

11. The method according to claim 10, wherein said physician record comprises one data selected from the group consisting of: promotional data, certification data, advertisement data, experience data, and any combination thereof.

12. The method according to claim 7 further comprising:

issuing an alert on said first access device to image said lesion at a predetermined time interval from initial imaging of said lesion.

13. The method according to claim 7, wherein said second record comprises data selected from the group consisting of: a preliminary treatment directive and a preliminary diagnosis, the method further comprising:

transmitting said second record from said second database to said first access device via said computer network.

14. The method according to claim 7, further comprising:

associating said first record and said second record with a patient profile, said patient profile comprising at least one data selected from the group consisting of: skin type data, medical allergies data, current medications data, symptoms of a disease data, lesion data, and any combination thereof; and storing said patient profile.

15. The method according to claim 7, further comprising:

generating a frame from said image data, said frame comprising transparent image data having anatomical landmarks; and superimposing said frame on said first access device to align subsequent image data.

16. The method according to claim 7, further comprising:

transmitting an identification label for a specimen container and a mailing label for said specimen container via said computer network from said third access device to at least one device selected from the group of devices comprising: said first access device and said second access device.

17. A non-transitory storage medium in which instructions are stored, which instructions, when read by a processor, cause said processor to:

image a lesion with a first access device of a patient to form a first image data;

provide a digital body map having an anatomical marker to said first access device;

associate said anatomical marker with said image data of said lesion, thus yielding a first record;

transmit said first record from said first access device via a network to a first database;

store said first record in said first database;

transmit said first record from said first database to a second access device;

attach said physician data to said first record via said second access device, thus yielding a second record, wherein said physician data comprises at least a second image data of said lesion taken at said physician's office and is at least one selected from the group consisting of: a preliminary diagnosis, and a preliminary treatment directive data;

transmit said second record to a second database;

store said second record in said second database;

with a third access device of a dermatopathologist in communication with said second database, retrieve said second record from said second database via said network; and attach dermatopathologist data to said second record, said dermatopathologist data comprises a third image data of a photomicrography of a biopsy of said lesion and a diagnosis based upon said first and second records, as well as a biopsy of said lesion, thus yielding a third record that is transmitted via said network to a third database and stored, and wherein said third record is accessible by said first and second access devices.

* * * * *